(12) United States Patent
Kim et al.

(10) Patent No.: US 9,120,718 B1
(45) Date of Patent: Sep. 1, 2015

(54) METHOD FOR PREPARING ALLYL ALCOHOL

(71) Applicant: LG CHEM, LTD., Seoul (KR)

(72) Inventors: Dae Sung Kim, Daejeon (KR); Won Jae Lee, Daejeon (KR); Myungjin Kong, Daejeon (KR); Yong-Jin Choe, Daejeon (KR); Hyun Nam, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/431,648

(22) PCT Filed: Jun. 27, 2014

(86) PCT No.: PCT/KR2014/005754
§ 371 (c)(1),
(2) Date: Mar. 26, 2015

(87) PCT Pub. No.: WO2014/209063
PCT Pub. Date: Dec. 31, 2014

(30) Foreign Application Priority Data

Jun. 27, 2013 (KR) .................. 10-2013-0074507
May 22, 2014 (KR) .................. 10-2014-0061369
Jun. 27, 2014 (KR) .................. 10-2014-0079572

(51) Int. Cl.
*C07C 27/00* (2006.01)
*C07C 29/00* (2006.01)
*C07C 29/147* (2006.01)

(52) U.S. Cl.
CPC .................. *C07C 29/147* (2013.01)

(58) Field of Classification Search
CPC ...... C07C 33/423; C07C 33/03; C07C 29/128
USPC ............................... 568/902, 909.5
See application file for complete search history.

(56) References Cited

U.S. PATENT DOCUMENTS

| | | | |
|---|---|---|---|
| 4,072,727 | A | 2/1978 | Vanderspurt |
| 5,892,066 | A | 4/1999 | Grey |
| 7,396,962 | B1 | 7/2008 | Dubois et al. |
| 7,655,818 | B2 | 2/2010 | Dubois et al. |
| 7,683,220 | B2 | 3/2010 | Matsunami et al. |
| 7,718,829 | B2 | 5/2010 | Masaaki et al. |
| 7,951,978 | B2 | 5/2011 | Arita et al. |
| 8,273,926 | B2 | 9/2012 | Bergman et al. |
| 2009/0287004 | A1 | 11/2009 | Bergman et al. |

FOREIGN PATENT DOCUMENTS

| | | |
|---|---|---|
| JP | 2012232903 | 11/2012 |
| KR | 1020130043606 | 4/2013 |
| WO | 2008092115 A1 | 7/2008 |
| WO | 2011108509 A1 | 9/2011 |

OTHER PUBLICATIONS

Jing Yi, et al., "Rhenium-Catalyzed Transfer Hydro-genation and Deoxygenation of Biomass-Derived Polyols to Small and Useful Organics," Chemsuschem., 2012, vol. 5, pp. 1401-1404.

Mika Shiramizu, et al., "Deoxygenation of Biomass-Derived Feedstocks: Oxorhenium-Catalyzed Deoxydehydration of Sugars and Sugar Alcohols," Angewandte, Chem. Int. Ed, 2012, vol. 51, pp. 8082-8086.

Oliver Kamm, et al., "Allyl Alcohol," Organic Syntheses, vol. 1, pp. 1941, year, 1941.

*Primary Examiner* — Jafar Parsa
(74) *Attorney, Agent, or Firm* — Dentons US LLP

(57) ABSTRACT

Disclosed is a method for preparing allyl alcohol, wherein glycerol and formic acid are reacted under specific synthesis conditions, thus remarkably increasing the concentration of allyl alcohol in the liquid reaction products and minimizing the production of allyl formate byproduct and the production of unreacted formic acid.

8 Claims, 3 Drawing Sheets

METHOD FOR PREPARING ALLYL ALCOHOL

This application is a National Stage Application of International Application No. PCT/KR2014/005754, filed Jun. 27, 2014, and claims the benefit of Korean Patent Application No. 10-2013-0074507, filed Jun. 27, 2013, Korean Patent Application No. 10-2014-0061369, filed May 22, 2014, and Korean Patent Application No. 10-2014-0079572, filed Jun. 27, 2014, all of which are hereby incorporated by reference in their entirety for all purposes as if fully set forth herein.

TECHNICAL FIELD

The present invention relates to a method for preparing allyl alcohol and, more particularly, to a novel method for preparing allyl alcohol, wherein glycerol and formic acid are reacted under specific synthesis conditions so as to drastically increase the concentration of allyl alcohol in liquid reaction products and minimize an allyl formate byproduct and the production of unreacted formic acid. This application claims the benefit of Korean Patent Application Nos. KR 10-2013-0074507, filed Jun. 27, 2013, KR 10-2014-0061369, filed May 22, 2014, and KR 10-2014-0079572, filed Jun. 27, 2014, which are hereby incorporated by reference in their entirety into this application.

BACKGROUND ART

Allyl alcohol is the simplest unsaturated alcohol represented by $CH_2=CHCH_2OH$, and is employed as a pesticide or is importantly utilized as a feed material or an intermediate in the course of producing many compounds. Furthermore, it may be used as an antiseptic, or applied in a variety of fields, including preparation of phthalic acid ester useful as a polymer plasticizer, preparation of butane-1,4-diol as a monomer of polyester (PBT), or production of acrylic acid.

Thorough research is ongoing into preparation of allyl alcohol, including reacting propylene, acetic acid and oxygen to give allyl acetate that is then hydrolyzed into allyl alcohol based on petrochemical processes. Also, as for eco-friendly preparation processes of allyl alcohol using bio materials compared to conventional petrochemical processes, when glycerol is reacted with formic acid, allyl alcohol may be obtained at high yield even in the absence of a catalyst, which is disclosed in U.S. Pat. No. 8,273,926. Useful as the material for allyl alcohol in such a registered patent, glycerol is a byproduct mainly resulting from preparation of biodiesel, and is currently utilized as a material for medical or cosmetic products, a solvent or lubricant. Since the supply of a glycerol byproduct is expected to increase in proportion to an increase in production of biodiesel, new applications, in addition to conventional glycerol uses, are under study. However, in order to maximize the yield of allyl alcohol in the above patent, formic acid has to be excessively added (e.g. 1.45 equivalents) relative to glycerol. In this case, the present inventors expect that the drawbacks such as long reaction time and complicated processing steps may occur, despite high allyl alcohol yield. As illustrated in FIG. 1, due to excessive use of formic acid and low product selectivity of allyl alcohol, gas phase products obtained via (a) according to a conventional technique include $CO_2$, $H_2O$ (W, by 100° C.), allyl formate (AF, by 80~83° C.), and allyl alcohol (AA, by 97° C.), with a large amount of unreacted formic acid (FA, by 100.8° C.). Also, allyl alcohol in the liquid reaction products obtained from (b) through a gas separator has a low concentration, undesirably increasing energy and cost required for the separation process thereof. Since the difference of boiling points of W, AA and FA as the gas phase products is very small, it is impossible to separate such products via typical distillation. Furthermore, due to the azeotropes of formic acid-water (FA-W) and allyl alcohol-formic acid-water (AA-FA-W), it is very difficult to separate formic acid from these products. Hence, in order to prepare allyl alcohol on a commercial scale, the liquid reaction products should contain allyl alcohol in a large amount and also the production of allyl formate byproduct and the production of unreacted formic acid should be minimized, and thereby it is possible to easily perform the subsequent separation process. Accordingly, there is a need for a novel synthesis method able to drastically increase the concentration of allyl alcohol from glycerol under specific synthesis conditions.

DISCLOSURE

Technical Problem

The present invention has been made keeping in mind the above problems in the related art, and an object of the present invention is to provide a novel method for preparing allyl alcohol, wherein specific synthesis conditions are applied so that the concentration of allyl alcohol in the liquid reaction products may be drastically increased and the production of allyl formate byproduct and the production of unreacted formic acid may be minimized.

Technical Solution

In order to accomplish the above object, the present invention provides a method for preparing allyl alcohol, comprising: a) adding glycerol with formic acid in an amount of 0.4~1.2 equivalents relative to 1 equivalent of glycerol and then increasing a reaction temperature to 220~240° C. from room temperature at a heating rate of at least 2.0° C./min in an inert gas atmosphere so that glycerol and formic acid are reacted; and b) condensing gas reaction products obtained in a), thus separating liquid reaction products including allyl alcohol therefrom.

Advantageous Effects

According to the present invention, a method for preparing allyl alcohol employs specific synthesis conditions so that the concentration of allyl alcohol in liquid reaction products can be drastically increased and an allyl formate byproduct and the production of unreacted formic acid can be minimized, making it possible to produce allyl alcohol on a commercial scale.

BEST MODE

Hereinafter, a detailed description will be given of a method for preparing allyl alcohol and allyl alcohol prepared thereby, according to the present invention.

The present invention addresses a method of mainly producing allyl alcohol, wherein specific synthesis conditions are applied so that the concentration of allyl alcohol in liquid reaction products may be remarkably increased and an allyl formate byproduct and the production of unreacted formic acid may be minimized. Therefore, allyl alcohol may be produced in a quite high concentration, compared to conventional methods.

To this end, the method for preparing allyl alcohol according to the present invention comprises: a) adding glycerol with formic acid in an amount of 0.4~1.2 equivalents relative to 1 equivalent of glycerol and then increasing a reaction temperature to 220~240° C. from room temperature at a heating rate of at least 2.0° C./min in an inert gas atmosphere so that glycerol and formic acid are reacted; and b) condensing a gas reaction products obtained in a), thus separating a liquid reaction products including allyl alcohol therefrom.

Since glycerol and formic acid are reacted at 1:1, the equivalent ratio is defined as the same concept as a molar ratio in the present invention.

Figure 2:
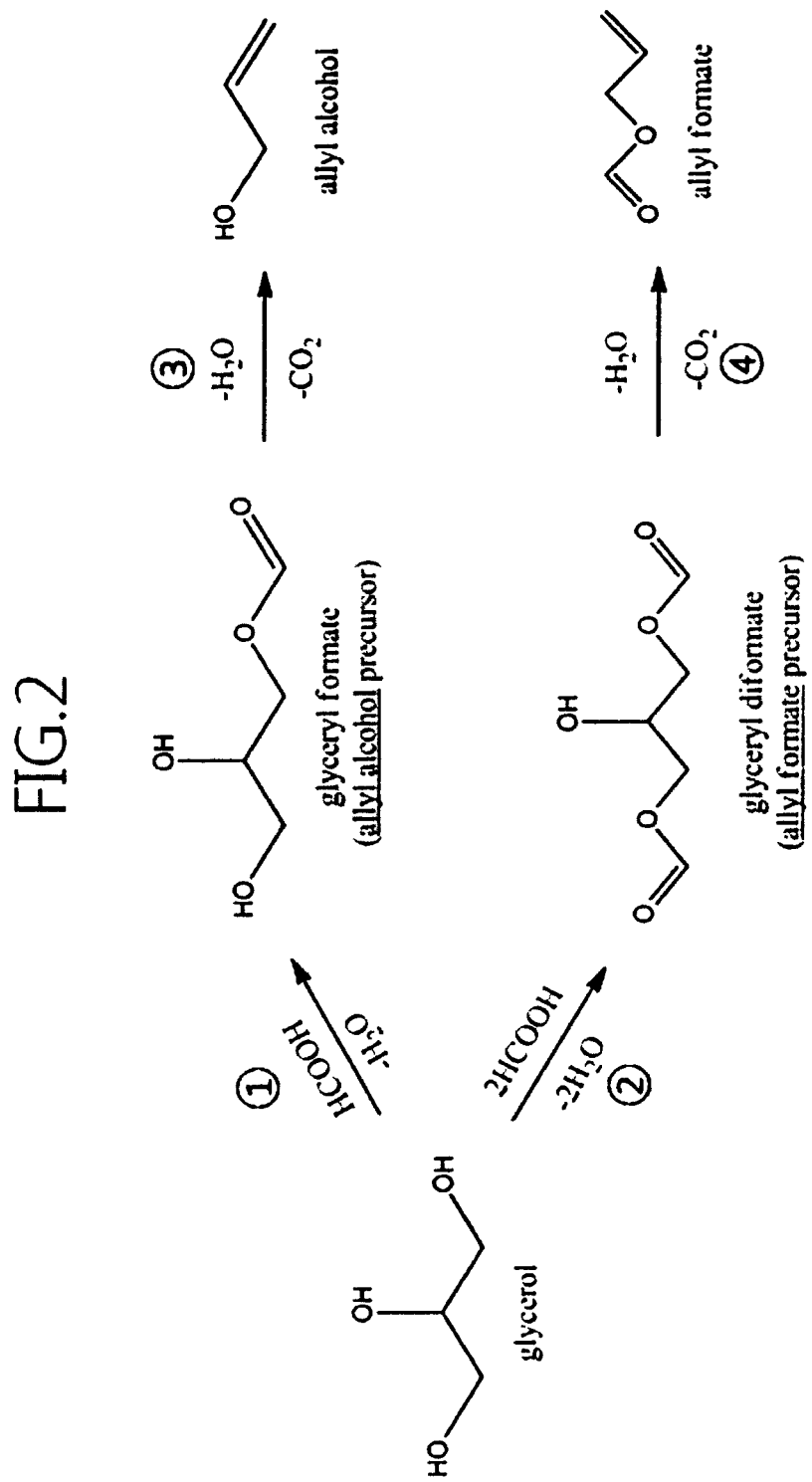
FIG. 2 illustrates a two-step reaction pathway for synthesizing allyl alcohol from glycerol.

Specifically, a two-step reaction for synthesizing allyl alcohol from glycerol is illustrated in FIG. 2. This reaction produces 1 mol allyl alcohol by sequentially eliminating 2 mol water from 1 mol glycerol. The first reaction step occurs by reacting 1 mol formic acid with 1 mol glycerol at low temperature, and the second reaction step takes place at high temperature in the presence of formic acid, converting 1 mol glyceryl formate, the allyl alcohol precursor, which is produced by the first reaction step. More specifically, in the first reaction step, 1 mol formic acid reacts with 1 mol glycerol, to produce 1 mol glyceryl formate, an allyl alcohol precursor, and 1 mol water. In the second reaction step, 1 mol glyceryl formate converts to 1 mol allyl alcohol at high temperature in the presence of formic acid, also producing 1 mol water and 1 mol carbon dioxide. In the second reaction step, the formic acid acts as a catalyst, rather than directly participating in the reaction.

In the first reaction step, when the heating time is increased or an excess of formic acid is added, a side reaction, No. 2 in FIG. 2, may occur. The side reaction may become dominant, and ultimately the production of an allyl formate byproduct may be increased.

Figure 3:
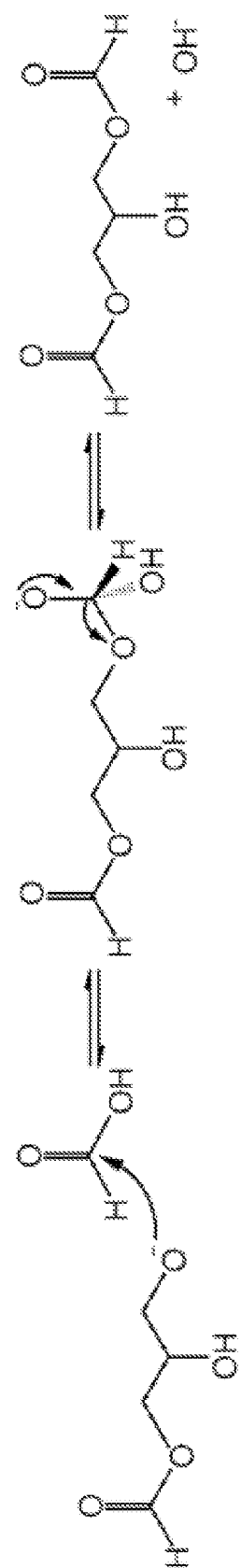
FIG. 3 illustrates a mechanism for esterification of glyceryl formate and formic acid.

The glyceryl formate, the first reaction step products, produced via reacting glycerol with formic acid, may undergo additional esterification. As illustrated in FIG. 3, when glyceryl formate reacts with formic acid, glyceryl diformate may be produced. This reaction is reversible.

In order to minimize the esterification producing glyceryl diformate from glyceryl formate obtained in the first reaction step, it is essential to prevent the reaction of glyceryl formate with an excess of formic acid and to maximally increase the heating rate to the temperature at which the second reaction step occurs. Specifically, when the production of glyceryl diformate, which is a side-reaction product, is reduced in the first reaction step, the selectivity of allyl alcohol may increase, thus ensuring the favorable effects for the subsequent separation process. The method for preparing allyl alcohol according to the present invention has the following features to drastically increase the concentration of allyl alcohol and to minimize the ally formate byproduct and the production of unreacted formic acid.

In the method for preparing allyl alcohol according to the present invention, any commercially available glycerol may be used without particular limitation so long as it is useful in preparation of allyl alcohol. Preferably useful is glycerol with a purity of 60~99.5%.

In the method for preparing allyl alcohol according to the present invention, any commercially available formic acid may be used without particular limitation so long as it is useful for the reaction with glycerol. In the present invention, formic acid may be added in an amount of 0.4~1.2 equivalents relative to 1 equivalent of glycerol. If the amount of formic acid is less than 0.4 equivalents, the amount of formic acid that may participate in the reaction is too small, and thus economic benefits may be negated. In contrast, if the amount thereof exceeds 1.2 equivalents, the amount of unreacted formic acid may increase and the production of allyl formate is increased due to side reactions, undesirably lowering the concentration of allyl alcohol in the liquid reaction products.

In the method for preparing allyl alcohol according to the present invention, glycerol and formic acid may be reacted by increasing the reaction temperature to 220~240° C. from room temperature at a heating rate of at least 2.0° C./min.

If the reaction temperature is lower than 220° C., the reaction of the glyceryl formate does not proceed to the next step. In contrast, if the reaction temperature is higher than 240° C., the production of allyl formate may be increased.

The heating rate from room temperature after addition of formic acid to glycerol in a) is set to at least 2.0° C./min, preferably 2.0~7.0° C./min, and more preferably 4.0~7.0° C./min. If the heating rate is less than 2.0° C./min, the production of glyceryl diformate becomes dominant in the first reaction step as shown in FIG. 2, undesirably increasing the production of allyl formate in the second reaction step.

Figure 1:
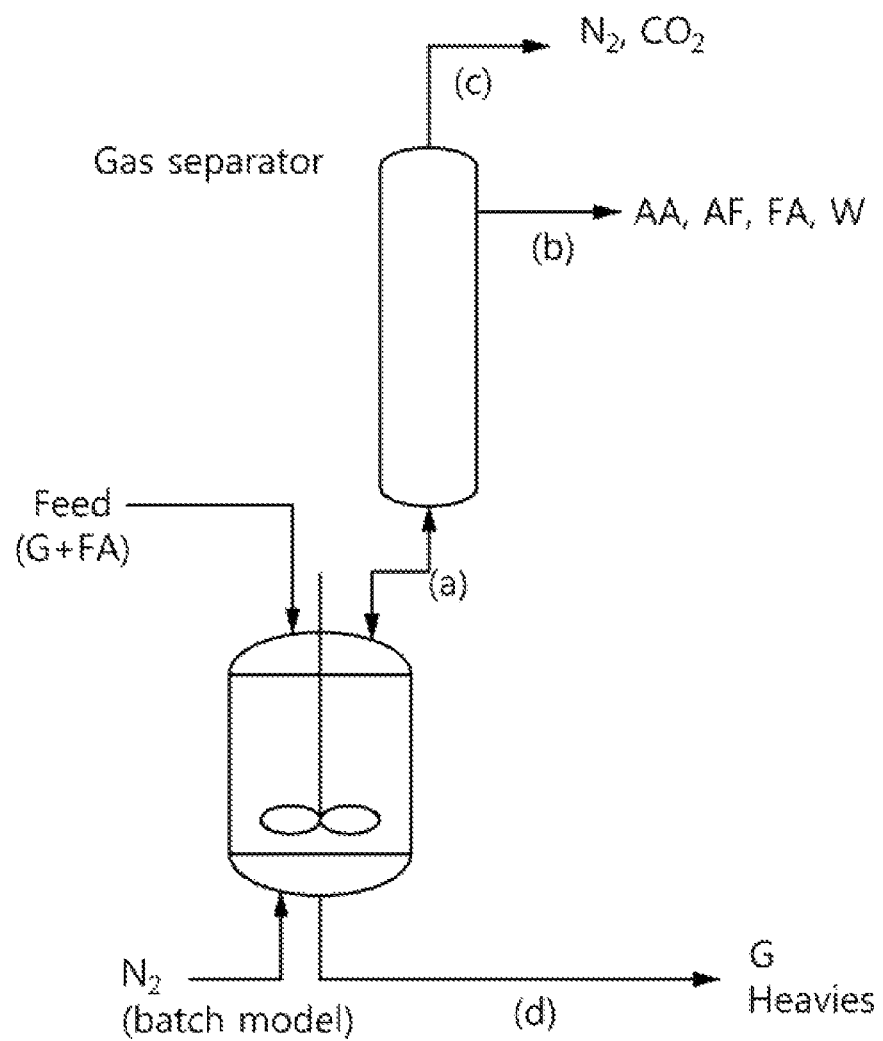
FIG. 1 illustrates a conceptual design for the preparation of allyl alcohol.

In the method for preparing allyl alcohol according to the present invention, the total reaction time including the heating time may be set to 7 h or less. If the total reaction time exceeds 7 h, the concentration of allyl alcohol in the liquid reaction products may be remarkably decreased. Furthermore, the separation of the liquid reaction products in b) may be carried out using a gas separator, as shown in the concept design for preparation of allyl alcohol in FIG. 1.

The inert gas may be any one selected from the group consisting of nitrogen, argon and helium, and the gas reaction products may include at least one selected from the group consisting of carbon dioxide, water vapor, allyl formate, allyl alcohol, and unreacted formic acid. The liquid reaction products may include at least one selected from the group consisting of allyl alcohol, allyl formate, unreacted formic acid, and water.

The concentration of allyl alcohol in b) is 40 wt % or more, and preferably 45 wt % or more, based on the total weight of the liquid reaction products, and thus economic benefits may be obtained and the production of allyl formate byproduct and the unreacted formic acid may be minimized, making it possible to prepare allyl alcohol on a commercial scale.

MODE FOR INVENTION

The following examples of the present invention are disclosed for illustrative purposes, but those skilled in the art will appreciate that various modifications, additions and substitutions are possible, without departing from the scope and spirit of the invention as disclosed in the accompanying claims.

Example 1

A 3-neck round-bottom flask was connected with a separation device having a gas separator and a 1-neck round-bottom flask. To measure the inner temperature of the reactor, one of the necks of the 3-neck round-bottom flask was provided with a thermocouple 1. In the 3-neck round-bottom flask, 202.6 g of glycerol and formic acid in an amount corresponding to 0.6 equivalents based on the molar ratio were placed, and the temperature of the reactants were increased to 230° C. at a heating rate of 4.2° C./min using a sand bath in a nitrogen atmosphere. As the reaction progressed, gas reaction products were generated from the liquid reactants, and then passed through the gas separator connected to the reactor, after which only the liquid reaction products were collected in the 1-neck round-bottom flask provided to the end of the gas separator. The reaction was not terminated until it passed 4.2 h after the reaction temperature was reached, and the reactor was cooled, after which the liquid reaction products collected in the flask was quantitatively analyzed using gas chromatography. Furthermore, quantitative analysis of unreacted glycerol remaining in the reactor was carried out using gas chromatography. The concentration of allyl alcohol in the liquid reaction products was measured to be 50.9 wt %.

Example 2

A 3-neck round-bottom flask was connected with a separation device having a gas separator and a 1-neck round-bottom flask. To measure the inner temperature of the reactor, one of the necks of the 3-neck round-bottom flask was provided with a thermocouple 1. In the 3-neck round-bottom flask, 27.6 g of glycerol and formic acid in an amount corresponding to 1 equivalent based on the molar ratio were placed, and the temperature of the reactants was increased to 230° C. at a heating rate of 5° C./min using a sand bath in a nitrogen atmosphere. As the reaction progressed, gas reaction products were generated formed from the liquid reactants, and then passed through the gas separator connected to the reactor, after which only the liquid reaction products were collected in the 1-neck round-bottom flask provided to the end of the gas separator. The reaction was not terminated until it passed 2.3 h after the reaction temperature was reached, and the reactor was cooled, after which the liquid reaction products collected in the flask was quantitatively analyzed using gas chromatography. Furthermore, quantitative analysis of unreacted glycerol remaining in the reactor was carried out using gas chromatography. The concentration of allyl alcohol in the liquid reaction products was measured to be 48.5 wt %.

Comparative Example 1

This comparative example was conducted under the same conditions as in Example 1, with the exception that the heating rate was 1.3° C./min. 2.8 h after reached the reaction temperature, the reaction was terminated, and the reactor was cooled, after which the liquid reaction products collected in the flask was quantitatively analyzed using gas chromatography. Furthermore, quantitative analysis of unreacted glycerol remaining in the reactor was performed using gas chromatography. As such, the concentration of allyl alcohol in the liquid reaction products was measured to be 38.0 wt %, which is lower than the concentration of allyl alcohol in the examples.

Comparative Example 2

This comparative example was conducted under the same conditions as in Example 1, with the exception that the heating rate was 1.3° C./min. To evaluate the effect of the reaction time at high temperature, 8 h after reached the reaction temperature, the reaction was terminated, and the reactor was cooled, after which the liquid reaction products collected in the flask was quantitatively analyzed using gas chromatography. Furthermore, quantitative analysis of unreacted glycerol remaining in the reactor was performed using gas chromatography. As such, the concentration of allyl alcohol in the liquid reaction products was measured to be 37.3 wt %, which is lower than the concentration of allyl alcohol in the examples.

The test results depending on the heating rate among the reaction conditions of Examples 1 and 2 and Comparative Examples 1 and 2 are shown in Table 1 below.

TABLE 1

| | FA Equivalent | Reaction Temp. (° C.) | Heating rate (° C./min) | Total reaction time (including heating time, h) | AA wt % |
|---|---|---|---|---|---|
| Ex. 1 | 0.6 | 230 | 4.2 | 5 | 50.9 |
| Ex. 2 | 1.0 | 230 | 5.0 | 3 | 48.5 |
| C. Ex. 1 | 0.6 | 230 | 1.3 | 5.5 | 38.0 |
| C. Ex. 2 | 0.6 | 230 | 1.3 | 10.5 | 37.3 |

As is apparent from Table 1, in both Examples 1 and 2 using the method for preparing allyl alcohol according to the present invention, the concentration of allyl alcohol was 40 wt % or more based on the total weight of the liquid reaction products, and was thus relatively high compared to Comparative Examples 1 and 2. Therefore, when allyl alcohol was prepared by the preparation method for Examples 1 and 2 according to the present invention, the concentration of allyl alcohol in the liquid reaction products was high and the allyl formate byproduct and the production of unreacted formic acid could be minimized.

DESCRIPTION OF THE REFERENCE NUMERALS IN THE DRAWINGS (a) pipeline for transporting vaporized mixture into gas separator from reactor
(b) pipeline for transporting condensed mixture removed from gas separator
(c) pipeline for transporting non-condensed mixture removed from gas separator
(d) pipeline for transporting unreacted material and products from bottom of reactor

The invention claimed is:
1. A method for preparing allyl alcohol, comprising:
a) adding glycerol with formic acid in an amount of 0.4~1.2 equivalents relative to 1 equivalent of glycerol and then increasing a reaction temperature to 220~240° C. from room temperature at a heating rate of at least 2.0° C./min in an inert gas atmosphere so that glycerol and formic acid are reacted; and
b) condensing gas reaction products obtained in a), thus separating liquid reaction products including allyl alcohol therefrom.
2. The method of claim 1, wherein the heating rate in a) is 2.0~7.0° C./min.
3. The method of claim 1, wherein the heating rate in a) is 4.0~7.0° C./min.
4. The method of claim 1, wherein the inert gas is any one selected from the group consisting of nitrogen, argon, and helium.
5. The method of claim 1, wherein the gas reaction products comprise at least one selected from the group consisting of carbon dioxide, water vapor, allyl formate, allyl alcohol, and unreacted formic acid.

6. The method of claim 1, wherein the liquid reaction products comprise at least one selected from the group consisting of allyl alcohol, allyl formate, unreacted formic acid, and water.

7. The method of claim 1, wherein the concentration of allyl alcohol in b) is 40 wt % or more based on a total weight of the liquid reaction products.

8. The method of claim 1, wherein the concentration of allyl alcohol in b) is 45 wt % or more based on a total weight of the liquid reaction products.

* * * * *